US00PP27745P3

(12) United States Plant Patent
Grosser

(10) Patent No.: US PP27,745 P3
(45) Date of Patent: Mar. 7, 2017

(54) ***CITRUS* ROOTSTOCK NAMED 'UFR-4'**

(50) Latin Name: [***Citrus reticulata*×*Citrus paradisi*)+*Citrus grandis*]×[*Citrus reticulata*+*Poncirus trifoliata* (trifoliate orange)**]
Varietal Denomination: UFR-4

(71) Applicant: Florida Foundation Seed Producers, Inc., Marianna, FL (US)

(72) Inventor: Jude W. Grosser, Winter Haven, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 14/544,424

(22) Filed: Jan. 5, 2015

(65) Prior Publication Data

US 2015/0195974 P1 Jul. 9, 2015

Related U.S. Application Data

(60) Provisional application No. 61/923,576, filed on Jan. 3, 2014.

(51) Int. Cl.
*A01H 5/08* (2006.01)

(52) U.S. Cl.
USPC ..... Plt./201

(58) Field of Classification Search
USPC ..... Plt./201
CPC ..... A01H 5/0806
See application file for complete search history.

(56) References Cited

U.S. PATENT DOCUMENTS

PP21,535 P2 11/2010 Grosser

OTHER PUBLICATIONS

Florida Foundation Seed Producers, Inc.; 9 New Citrus Rootstocks—Descriptions and Data; May 2014, 14 pages.*
U.S. Appl. No. 14/544,427, filed Jan. 5, 2015, Grosser.
U.S. Appl. No. 14/544,423, filed Jan. 5, 2015, Grosser.
U.S. Appl. No. 14/544,572, filed Jan. 22, 2015, Grosser.
U.S. Appl. No. 14/544,571, filed Jan. 22, 2015, Grosser.
U.S. Appl. No. 14/544,573, filed Jan. 22, 2015, Grosser.
U.S. Appl. No. 14/545,063, filed Mar. 20, 2015, Grosser.
U.S. Appl. No. 14/544,570, filed Jan. 22, 2015, Grosser.
U.S. Appl. No. 14/544,425, filed Jan. 5, 2015, Grosser.
Grosser et al., "Protoplast fusion and citrus improvement," *Plant Breeding Reviews* 8:339-374, 1990.
Grosser et al., "Development of "tetrazyg" rootstocks tolerant of the diaprepes/phytophthora complex under greenhouse conditions," *Proc. Fla. State Hort. Soc.* 116:263-267, 2003.
Grosser et al., "Continued Development of Rootstocks Tolerant of the *Phytophthora*-Diaprepes Complex via Greenhouse Screening," *Proc. Fla. State Hort. Soc.* 120:103-109, 2007.
Grosser et al., "Protoplast fusion for production of tetraploids and triploids: Applications for scion and rootstock breeding in citrus," *Plant Cell Tissue Organ Culture* 104:343-357, 2011.
Letter and corresponding informational document to Florida citrus nurseries for the purpose of a possible license agreement, dated Jan. 9, 2014.

* cited by examiner

*Primary Examiner* — Kent L Bell
(74) *Attorney, Agent, or Firm* — Dentons US LLP

(57) ABSTRACT

'UFR-4' is a new and distinct allotetraploid *citrus* rootstock for tree size control and improved disease resistance. 'UFR-4' has shown a positive reaction to the Huanglongbing disease (HLB, or *citrus* greening disease) in multiple experimental field trials. Scion trees grafted on this rootstock show a reduced frequency of infection and reduced disease symptoms once infected when compared to commercial diploid rootstocks. 'UFR-4' rootstock also showed tolerance to the *Diaprepes/Phytophthora* complex in greenhouse tests.

6 Drawing Sheets

Latin name of the genus and species of the plant claimed: allotetraploid hybrid of [(*Citrus reticulata*×*Citrus paradisi*)+*Citrus grandis*]×[*Citrus reticulata*+*Poncirus trifoliata* (trifoliate orange)].

Variety denomination: 'UFR-4'.

BACKGROUND OF THE INVENTION

The present invention relates to a new and distinct variety of *citrus* rootstock named 'UFR-4'. The Plant Improvement Team in Lake Alfred, Fla. has pioneered the development and testing of allotetraploid *citrus* rootstocks. 'UFR-4' is an allotetraploid zygotic hybrid derived from a conventional cross of two somatic hybrids previously produced by protoplast fusion. The somatic hybrid seed parent is 'Nova' mandarin hybrid+'Hirado Buntan' pummelo (zygotic seedling), and the somatic hybrid pollen parent is 'Cleopatra' mandarin+'Argentine' trifoliate orange.

BRIEF SUMMARY OF THE INVENTION

'UFR-4' was selected on the basis of its positive reaction to the Huanglongbing disease (HLB, or *citrus* greening disease) in multiple experimental field trials. The claimed plant was first asexually reproduced by grafting to 'Swingle' citrumelo and 'Volkameriana' rootstocks and planted in Lake Alfred, Fla. The resulting trees were true to type. Scion trees grafted on this rootstock show a reduced frequency of infection, and reduced disease symptoms once infected as compared to commercial diploid rootstocks. Although trees grafted to 'UFR-4' grow off quickly, trees remain medium in size, comparable to trees grafted to 'Swingle' citrumelo rootstock. Trees are smaller on flatwoods soils. 'UFR-4' is seedy and polyembryonic, making it amenable to standard nursery propagation practices for uniform liner production. This selection has shown tolerance to the *Diaprepes/Phytophthora* complex in greenhouse tests. Long-term performance of scion trees grafted on 'UFR-4' is unknown. Yield and fruit quality data is limited, but 3 years of data from young trees (the St. Helena project, see Table 1) indicates good productivity and fruit quality. Tolerance to *citrus* blight is also unknown. Fruit quality for the 'Valquarius'® 'SF14W-62' (U.S. Plant Pat. No. 21,535) scion was significantly less than that of 'Vernia'.

TABLE 1

Rootstock Data from 5-year old trees in the St. Helena trial - Dundee, FL

| Scion | | Rootstock | Lbs Solids/Box 2012 | Lbs Solids/Box 2013 |
|---|---|---|---|---|
| 'VALQUARIUS' | Som. Hyb. | 'UFR-6' | 5.64 | 5.43 |
| 'VERNIA' | Som. Hyb. | 'UFR-6' | 5.67 | 6.01 |
| 'VALQUARIUS' | Tetrazyg | 'UFR-1' | 5.5 | 4.87 |
| 'VERNIA' | Tetrazyg | 'UFR-1' | 5.61 | 6.28 |
| 'VERNIA' | Tetrazyg | 'UFR-2' | 5.47 | 5.93 |
| 'VALQUARIUS' | Tetrazyg | 'UFR-2' | 4.57 | 5.37 |
| 'VALQUARIUS' | Tetrazyg | 'UFR-3' | 4.84 | 5.05 |
| 'VERNIA' | Tetrazyg | 'UFR-3' | 5.46 | 5.82 |
| 'VERNIA' | Tetrazyg | 'UFR-4' | 5.79 | 6.07 |
| 'VALQUARIUS' | Tetrazyg | 'UFR-4' | 4.65 | 5.07 |
| 'VALQUARIUS' | Tetrazyg | 'UFR-5' | 5.76 | 5.72 |
| 'VERNIA' | Tetrazyg | 'UFR-5' | 5.89 | 5.34 |
| 'VALQUARIUS' | Diploid | 'FG 1731' | 5.83 | 6.81 |
| 'VALQUARIUS' | Diploid | 'FG 1731' | 5.12 | 5.63 |
| 'VERNIA' | Diploid | 'SWINGLE'* | 5.11 | 5.79 |
| 'VALQUARIUS' | Diploid | 'SWINGLE'* | NS | 5.61 |
| 'VERNIA' | Diploid | 'CLEO'* | 4.79 | 5.51 |
| 'VALQUARIUS' | Diploid | 'CLEO'* | NS | 5.21 |
| 'VERNIA' | Diploid | 'R. LEMON'* | 3.67 | na |
| 'VALQUARIUS' | Diploid | 'VOLK'* | NS | 4.12 |
| 'VERNIA' | Diploid | 'VOLK'* | 3.6 | 4.73 |
| 'VALQUARIUS' | Diploid | 'KUHARSKE'* | NS | 5.75 |
| 'VERNIA' | Diploid | 'KUHARSKE'* | 4.34 | 5.83 |

| Scion | Yield Boxes/Tree 2011 (35 mo.) | Yield Boxes/Tree 2012 (47 mo.) | Yield Boxes/Tree 2013 (59 mo.) | Cumulative Yield (Boxes) |
|---|---|---|---|---|
| 'VALQUARIUS' | 0.5 | 0.78 | 1.94 | 3.22 |
| 'VERNIA' | 0.4 | 0.63 | 1.41 | 2.44 |
| 'VALQUARIUS' | NS | 0.72 | 2.23 | 2.95 |
| 'VERNIA' | 0.31 | 0.67 | 1.33 | 2.31 |
| 'VERNIA' | 0.35 | 0.25 | 1.38 | 1.98 |
| 'VALQUARIUS' | NS | 0.75 | 1.73 | 2.48 |
| 'VALQUARIUS' | NS | 0.81 | 1.97 | 2.78 |
| 'VERNIA' | 0.37 | 0.38 | 1.82 | 2.57 |
| 'VERNIA' | 0.54 | 0.71 | 1.73 | 2.98 |
| 'VALQUARIUS' | NS | 0.65 | 1.59 | 2.64 |
| 'VALQUARIUS' | 0.33 | 0.56 | 1.80 | 2.69 |
| 'VERNIA' | 0.42 | 0.25 | 1.93 | 2.60 |
| 'VALQUARIUS' | NS | 0.68 | 2.20 | 2.88 |
| 'VALQUARIUS' | NS | 0.67 | 2.77 | 3.44 |
| 'VERNIA' | 0.33 | 0.85 | 1.08 | 2.26 |
| 'VALQUARIUS' | NS | NS | 1.50 | 1.50 |
| 'VERNIA' | NS | 0.50 | 0.83 | 1.33 |
| 'VALQUARIUS' | NS | NS | 1.7 | 1.7 |
| 'VERNIA' | NS | 0.78 | na | 0.78 |
| 'VALQUARIUS' | NS | NS | 2.58 | 2.58 |
| 'VERNIA' | 0.4 | 1.13 | 0.83 | 2.36 |

TABLE 1-continued

Rootstock Data from 5-year old trees in the St. Helena trial - Dundee, FL

| | | | | |
|---|---|---|---|---|
| 'VALQUARIUS' | NS | NS | 2.2 | 2.2 |
| 'VERNIA' | 0.15 | 0.75 | 1.08 | 1.98 |

NS — not significant fruit;
na — data not available;
*control commercial rootstock
One box contains 90 lbs. fruit

BRIEF DESCRIPTION OF THE DRAWINGS

'UFR-4' is illustrated by the accompanying photographs, which show the tree's form, foliage, and fruit. The colors shown are as true as can be reasonably obtained by conventional photographic procedures. The photographs are of a tree approximately 6-years old, growing on its own roots in Lake Alfred, Fla. All figures were taken in the fall of 2013.

DETAILED BOTANICAL DESCRIPTION

Figure 1:
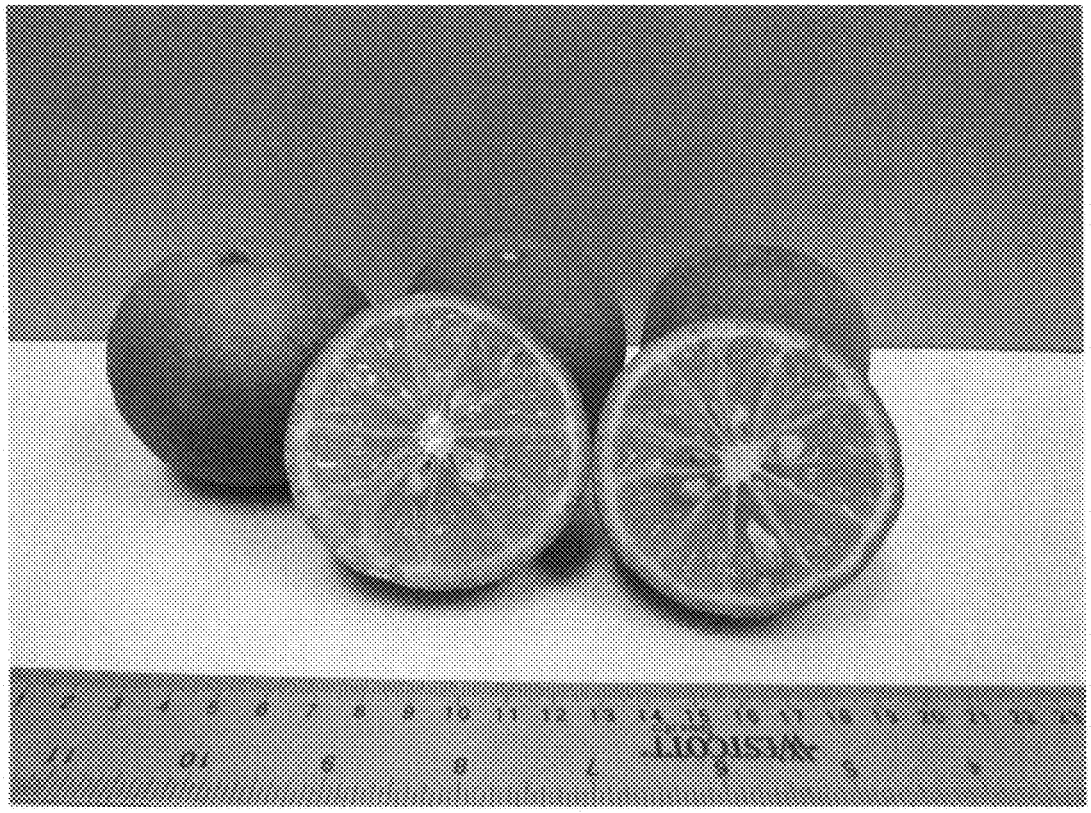
FIG. 1.—Shows a close-up of the nearly mature fruits with the rind and cross-sectional view of the fruit when cut in the center.
Figure 2:
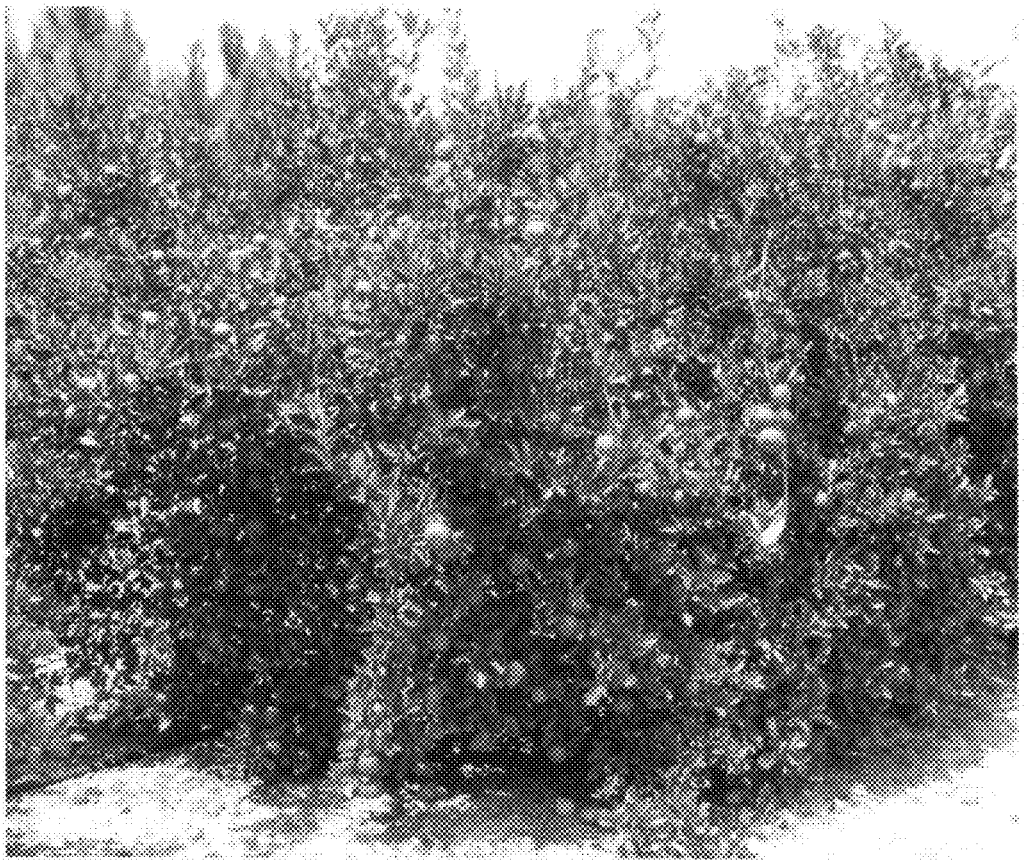
FIG. 2.—Shows the overall mature plant growth habit in the fall of 2013.
Figure 3:
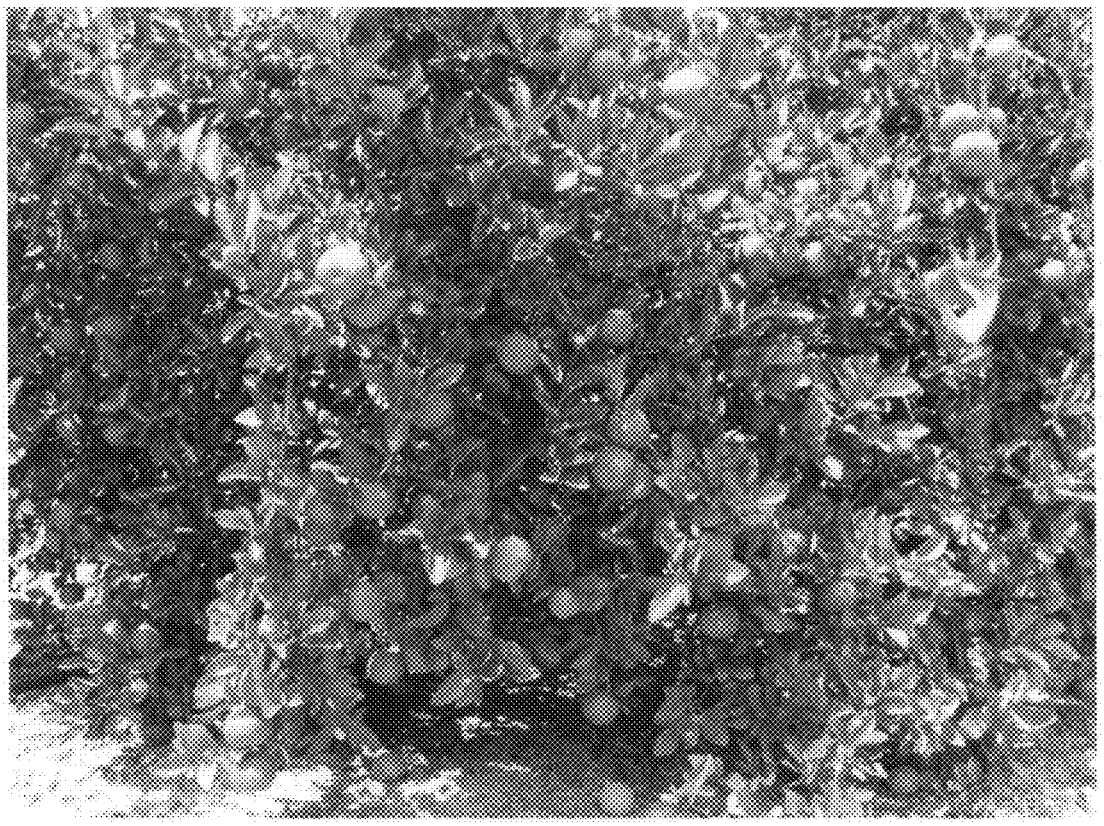
FIG. 3.—Shows nearly mature fruits hanging on the tree.
Figure 4:
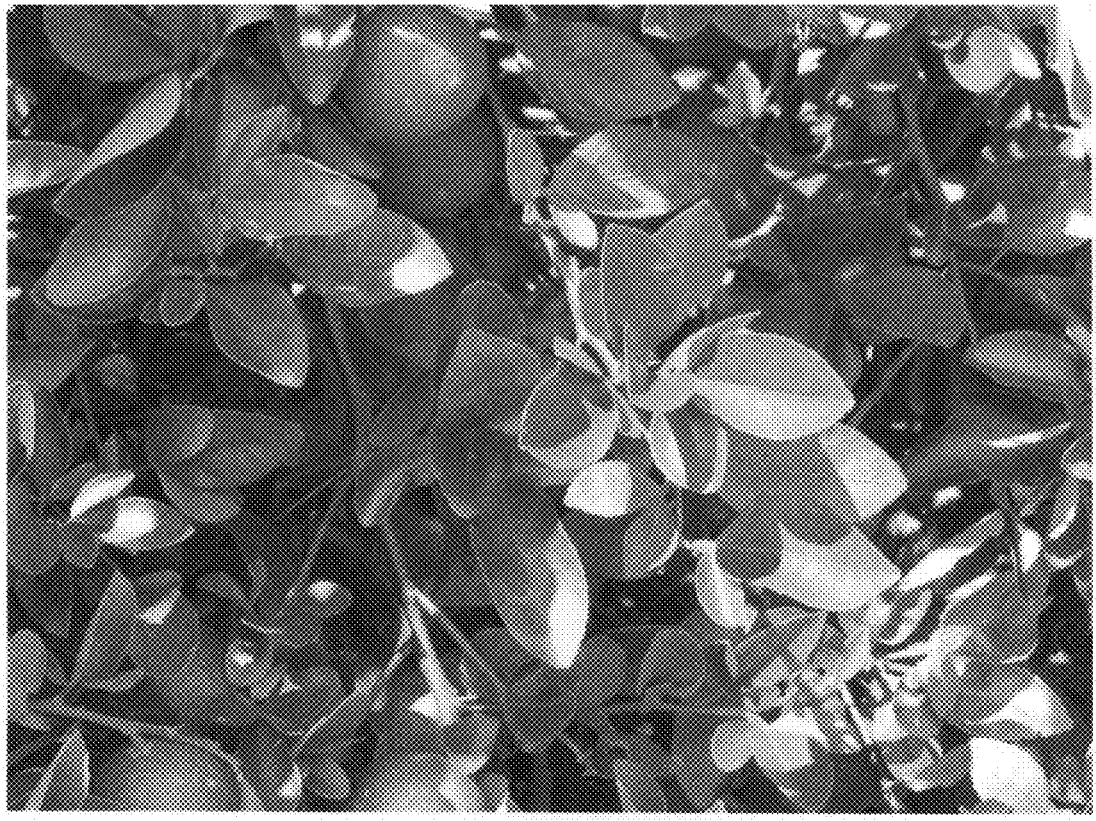
FIG. 4.—Shows a close-up of leaves and nearly mature fruits.
Figure 5:
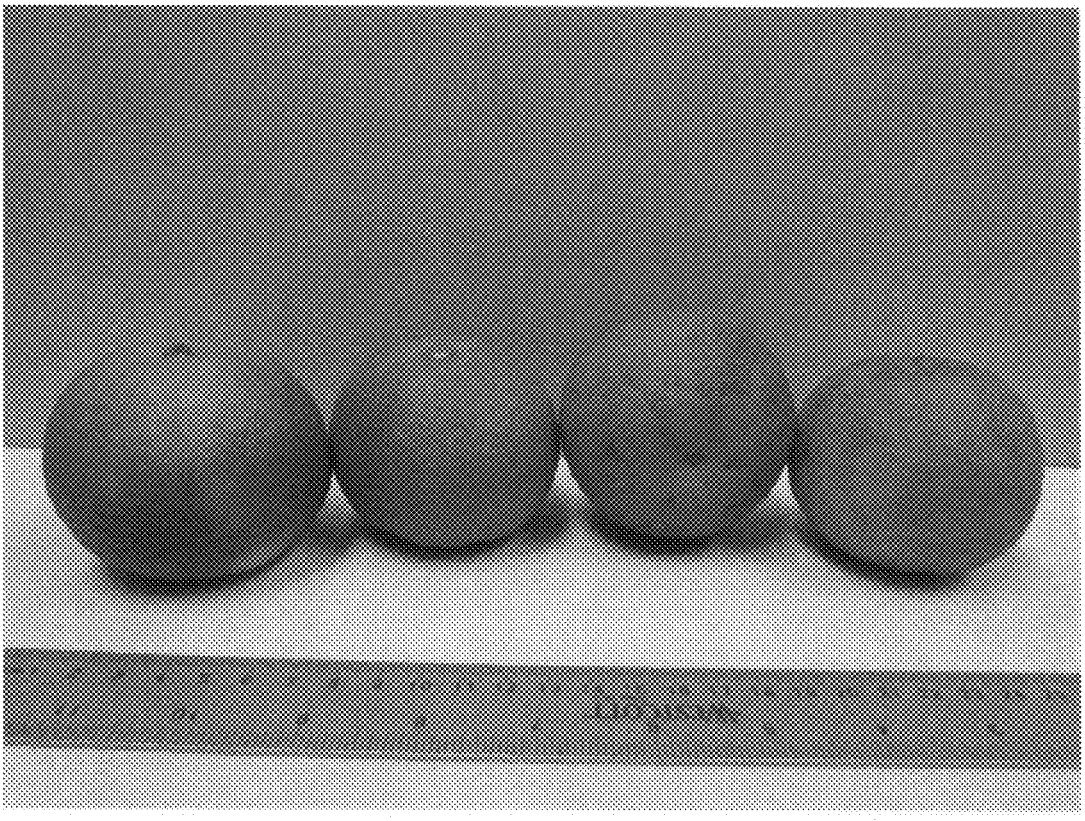
FIG. 5.—Shows a close-up of nearly mature fruits.
Figure 6:
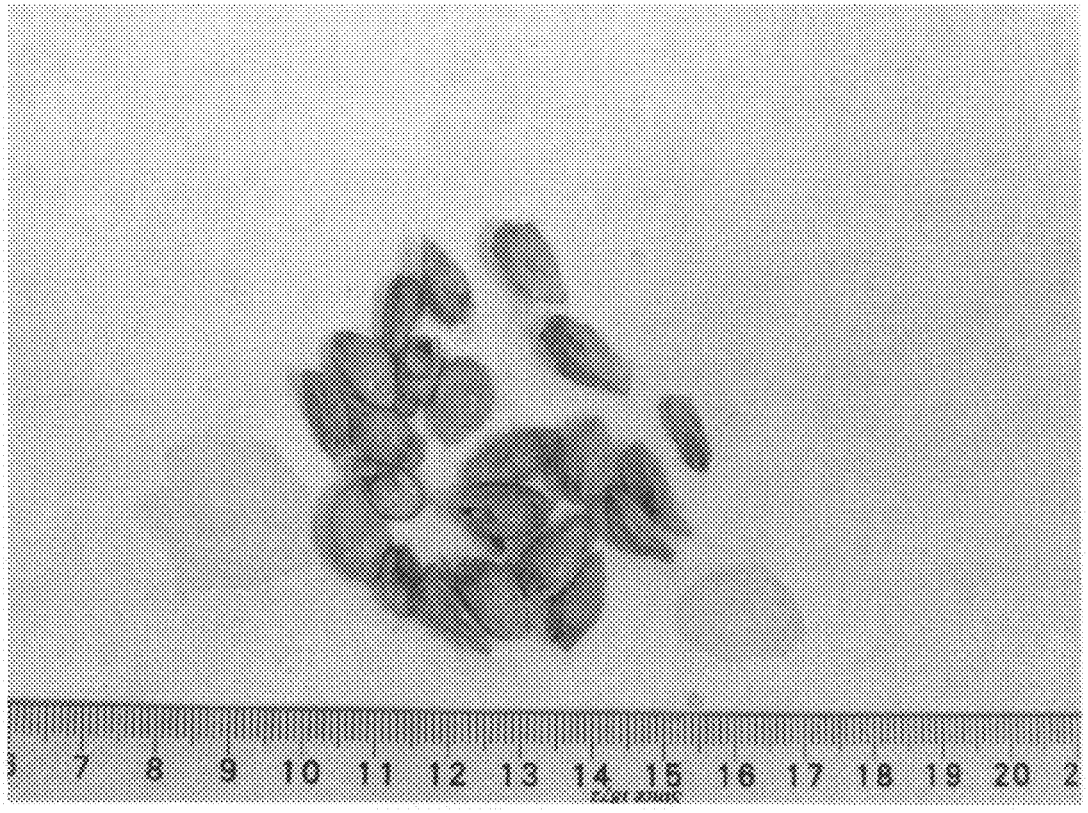
FIG. 6.—Shows a close-up of seeds from nearly mature fruit.

The following detailed description sets forth the distinctive characteristics of 'UFR-4'. The colors (except those in common terms) are described from R.H.S. Colour Chart published by The Royal Horticultural Society in London (second edition), in association with the Flower Council of Holland.

Phenotypic Description of *Citrus reticulata* 'UFR-4'.

Classification:

*Botanical.*—*[Citrus reticulata* hybrid ('Clementine' mandarin×'Orlando' tangelo) *Citrus reticulata*×*Citrus paradisi*)+*Citrus grandis]*×*[Citrus reticulata* +*Poncirus trifoliata* (trifoliate orange)].

*Common name.*—Complex allotetraploid 'tetrazyg' rootstock hybrid.

Parentage:

*Female parent.*—'Nova' mandarin+'Hirado Buntan' pummelo (zygotic seedling); unpatented somatic hybrid.

*Male parent.*—'Cleopatra' mandarin+'Argentine' trifoliate orange; unpatented somatic hybrid.

Tree:

*Ploidy.*—Tetraploid.

*Size.*—Medium.

*Height.*—3.07 meters.

*Tree spread.*—2.2 to 2.7 meters.

*Vigor.*—Vigorous.

*Density.*—Canopies are quite dense.

*Form.*—The tree has a rounded shaped with mostly lateral branches growing toward low to medium angles. Branches with fruit exhibit drooping.

*Growth habit.*—Mostly lateral growth with upright growth on the top.

Trunk:

*Trunk diameter.*—11 cm in diameter at 30 cm above the ground on a 6-year-old tree.

*Trunk texture.*—Smooth.

*Trunk bark color.*—RHS 198A (greyed-green); irregularly striated with RHS N189A (greyed-green).

Branches:

*Crotch angle.*—First crotch forms a 45- to 48-degree angle, middle crotch forms a 40-degree angle.

*Branch length.*—Branch reaches 2.3 meters from the first crotch to the tip of the branch.

*Branch texture.*—Relatively rough with small thorns or spines.

*Branch color* (*shoots from previous flush, hardened, and* 4 *to* 5 mm *in diameter*).—RHS 137A (green).

Leaves:

*Size* (*lamina average*).—Length: 87 mm. Width: 48 mm. L/W ratio: 1.81.

*Thickness.*—Thicker than average commercial diploid rootstock hybrids.

*Type.*—Mostly simple leaves, although trifoliate and bifoliate leaves also appear on the same tree.

*Shape.*—Elliptical.

*Apex.*—Retuse.

*Base.*—Acute to sub-obtuse.

*Margin.*—Entire and slightly undulate.

*Surface.*—Upper surface: Glabrous. Lower surface: Medium veins that are pinnately netted.

*Color.*—Upper surface (adaxial): RHS 137A (green). Lower surface (abaxial): RHS 137C (green).

*Petiole.*—Shape: Brevipetiolate (shorter than leaf lamina); junction between petiole and lamina is articulate. Width (petiole wing): Narrow. Shape (petiole wing): Obovate. Length: 16.4 to 16.5 mm. Width: 5.5 to 5.6 mm. Color: RHS N137A (green).

Flowers and flower buds:

*Type.*—Hermaphrodite.

*Bearing.*—Flowers grow from leaf axillaries and leaf terminals singly and in small clusters; most single flowers grow from leaf axillaries.

*Flower bud size.*—Shape: Initial visible flower bud has a round ball shape; mature flower bud has an elongated olive shape.

*Flower petals.*—Shape: Flat, spatula-shaped. Apex shape: Smooth, acute-shaped. Base shape: Even obtuse. Margin: Smooth.

*Flower sepal.*—Shape: Delta-shaped with an acute angle at the apex. Apex shape: Triangle-shaped. Margin: Smooth.

*Fragrance.*—Fragrant/Moderately fragrant.

*Reproductive organs.*—Fertility: Appears self-fertile. Pollen amount: Abundant/Moderately amount. Pollen color (general): Bright-yellow. Ovary shape: Oval-shaped.

Fruit:

*Size.*—Uniform.

*Height.*—62 to 65 mm on average.

*Width.*—74 to 76 mm on average.

*Average weight* (*per individual fruit*).—174 grams.

*Shape.*—Round.

*Shape* (*cross-section*).—Round.

*Apex.*—Truncated with slight dent.

*Apex cavity diameter.*—N/A.

*Base cavity diameter.*—6.6 to 6.9 mm.

*Base.*—No neck.

*Harvesting.*—Fruit can be harvested in September in Florida, and should be harvested no later than October, as trees have a tendency to drop fruit quickly into November.

*Fruit stem* (*short stem connecting the fruit*).—Length: 7.8 mm. Diameter: 5.5 mm. Color: RHS 138B (green) with RHS 195B (greyed-green) strip.

Rind:

*Adherence.*—Adherence between albedo (mesocarp) and flesh (endocarp) is medium. The adherence is evenly distributed from base to apex.

*Thickness.*—3.8 to 4.9 mm on average.

*Texture.*—Smooth.

*Color.*—Flavedo (epicarp): Range between RHS 150B (yellow-green) to RHS 154C (yellow-green). Albedo (mesocarp): RHS 10C (yellow).

*Stylar end.*—Closed.

*Rind oil cell density.*—176 oil cells/square cm.

Flesh:

*Number of segments.*—Between 11 and 12 segments per fruit on average.

*Segment walls.*—Medium-firm with sufficient strength to maintain integrity as separated.

*Juice.*—Abundant.

*Color.*—Uniformly RHS 153D (yellow-green).

*Texture.*—Medium soft.

*Vesicles.*—Length: Arranged from 14.3 to 15.2 mm on average. Diameter (thickness): 4.3 to 5.7 mm on average.

*Eating quality.*—N/A.

*Juice index.*—Soluble solids (average): 9.0 Brix.

Seeds:

*Type.*—Polyembryonic.

*Number.*—Ranges from 18 to 23. Occasionally some fruit contains less than 18 seeds.

*Shape.*—Seed shapes are not uniform. Normal seeds are mostly ventricose/swollen shaped and clavate club shaped.

*Size.*—Length: 11.5 to 13.5 mm. Width: 7.1 to 8.2 mm.

*Seed coat color.*—Outer Surface: RHS 155B (white) and wrinkled. Inner surface: RHS 165C (greyed-orange). Cotyledon color: RHS 155C (white).

What is claimed is:

1. A new and distinct *citrus* rootstock plant as illustrated and described herein.

* * * * *